US008802902B2

(12) United States Patent
Warner et al.

(10) Patent No.: US 8,802,902 B2
(45) Date of Patent: Aug. 12, 2014

(54) PRESSURE DRIVEN DISTILLATION FOR ETHANOL PRODUCTION AND RECOVERY FROM HYDROGENATION PROCESS

(75) Inventors: R. Jay Warner, Houston, TX (US); David Lee, Houston, TX (US); Adam Orosco, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 13/595,400

(22) Filed: Aug. 27, 2012

(65) Prior Publication Data

US 2013/0172630 A1    Jul. 4, 2013

Related U.S. Application Data

(60) Provisional application No. 61/581,794, filed on Dec. 30, 2011.

(51) Int. Cl.
*C07C 27/04* (2006.01)

(52) U.S. Cl.
USPC .......................................... 568/884

(58) Field of Classification Search
USPC .......................................... 568/884
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Paulik et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,352,940 A | 10/1982 | Adelman et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg |
| 5,124,004 A | 6/1992 | Grethlein et al. |
| 5,144,068 A | 9/1992 | Smith et al. |
| 5,149,680 A | 9/1992 | Kitson et al. |
| 5,185,476 A | 2/1993 | Gustafson |

(Continued)

FOREIGN PATENT DOCUMENTS

| | | |
|---|---|---|
| CN | 201768393 | 3/2011 |
| CN | 102091429 | 6/2011 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 826-840.
ZeaChem, Inc., Technology Overview, Lakewood, Colorado www.zeachem.com, 2008.
Witzeman and Agreda in "Acetic Acid and its Derivatives,", Marcel Dekker, NY, 1992, p. 271.
Subramani et al. "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Fereydoun G Sajjadi
*Assistant Examiner* — Kofi Adzamli (57) ABSTRACT

Recovery of alcohols, in particular ethanol, from a crude ethanol product obtained from the hydrogenation of acetic acid using pressure driven distillation to separate the crude ethanol product. The crude ethanol product may be fed to a distillations column in which a substantial portion of the water is removed with the acetic acid in the residue. A second column is at higher pressure than a first column.

18 Claims, 5 Drawing Sheets

(56) References Cited

U.S. PATENT DOCUMENTS

| | | |
|---|---|---|
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 * | 10/2004 | Colley et al. .......... 560/231 |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 2003/0013908 A1 | 1/2003 | Horan et al. |
| 2003/0077771 A1 | 4/2003 | Verser et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chornet et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Weiner et al. |
| 2010/0137630 A1 | 6/2010 | Garton et al. |
| 2010/0197485 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 102228831 | 11/2011 |
| CN | 102229520 | 11/2011 |
| EP | 0056488 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |

(56) References Cited

FOREIGN PATENT DOCUMENTS

| WO | WO 2009/048335 | | 4/2009 |
|---|---|---|---|
| WO | WO 2009/063174 | | 5/2009 |
| WO | WO 2009/063176 | | 5/2009 |
| WO | WO 2009063176 A1 | * | 5/2009 |
| WO | WO 2009/105860 | | 9/2009 |
| WO | WO 2010/014146 | | 2/2010 |
| WO | WO 2010/014151 | | 2/2010 |
| WO | WO 2010/055285 | | 5/2010 |
| WO | WO 2011/097227 | | 8/2011 |
| WO | WO 2012/006228 | | 1/2012 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

J. Jones, et al., "The Cativa™ Process for the Manufacture of Acetic Acid", Platinum Metals Review, vol. 44, No. 3, pp. 94-104 (Jul. 2000).

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Search Report and Written Opinion mailed Sep. 2, 2011 in corresponding International Application No. PCT/US2011/023276.

Written Opinion mailed May 8, 2012 in corresponding International Application No. PCT/US2011/023276.

International Preliminary Report on Patentability mailed Jun. 27, 2012 in corresponding International Application No. PCT/US2011/023276.

International Search Report and Written Opinion mailed Oct. 25, 2012 in corresponding International Application No. PCT/US2012/052511.

* cited by examiner

PRESSURE DRIVEN DISTILLATION FOR ETHANOL PRODUCTION AND RECOVERY FROM HYDROGENATION PROCESS

CROSS REFERENCE TO RELATED APPLICATION

This application claims priority to U.S. Provisional Application No. 61/581,794, filed Dec. 30, 2011, the entirety of which is incorporated herein by reference.

FIELD OF THE INVENTION

The present invention relates generally to processes for producing alcohols and, in particular, to a process for recovering ethanol produced by acetic acid hydrogenation using pressure driven distillation. Advantageously, this may allow recovery of anhydrous ethanol.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. Conventional processes to overcome the azeotrope involve using benzene or cyclohexane as an azeotrope agent or an adsorption unit, such as a molecular sieve. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising the steps of hydrogenating acetic acid from an acetic acid feed stream in a reactor to form a crude ethanol product comprising ethanol, ethyl acetate, acetic acid, and water; separating at least a portion of the crude ethanol product in a first column at a first pressure into a first distillate comprising ethanol, ethyl acetate, and low concentrations of water, and a first residue comprising acetic acid and water, and separating at least a portion of the first distillate in a second column at a second pressure to yield an ethanol product stream and an ethyl acetate stream, wherein the second pressure is higher than the first pressure. The second pressure may be greater than atmospheric pressure, e.g., greater than 200 kPa. In some embodiments, the second pressure may be from 200 kPa to 2,000 kPa. The first pressure may be less than 80 kPa and may range from 0.01 kPa to 80 kPa. The second pressure may be at least 100 kPa higher than the first pressure. In some embodiments, at least 60% of the water, e.g., at least 80% of the water in the crude ethanol product is removed in the first residue stream. The low concentration of water may be less than 4.5 wt. %. The first distillate may comprise from 20 to 90 wt. % ethanol, from 0.01 to 4 wt. % water, from 0.01 to 60 wt. % ethyl acetate and less than 0.5 wt. % acetic acid, e.g., less than 600 wppm acetic acid. The first residue may comprise from 2.5 to 40 wt. % acetic acid, from 60 to 99 wt. % water, and less than 0.5 wt. % ethanol. When the first residue comprises from 0.01 to 10 wt. % acetic acid, the process may further comprise the step of neutralizing or reacting the acetic acid from the first residue. In some embodiments, no azeotropic agents and/or entrainers are added to the first column or to the second column. The ethanol product stream may comprise less than 1.5 wt. % ethyl acetate, less than 1 wt. % acetic acid, from 96 to 99.5 wt. % ethanol and from 0.01 to 4 wt. % water. Acetic acid may be recovered from the first residue and returned to the reactor. The ethyl acetate stream and at least a portion of the water stream may also be returned to the reactor. In some embodiments, the crude ethanol product, the first distillate, and/or the ethanol product stream are not dehydrated using an adsorption unit or membrane. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a second embodiment, the present invention is directed to a process for producing ethanol comprising the steps of providing a crude ethanol product comprising ethanol, ethyl acetate, acetic acid, and water; separating at least a portion of the crude ethanol product in a first column at a first pressure into a first distillate comprising ethanol, ethyl acetate, and low concentrations of water, and a first residue comprising acetic acid and water, and separating at least a portion of the first distillate in a second column at a second pressure to yield an ethanol product stream and an ethyl acetate stream, wherein the second pressure is higher than the first pressure.

In a third embodiment, the present invention is directed to a process for producing ethanol comprising the steps of hydrogenating acetic acid from an acetic acid feed stream in a reactor to form a crude ethanol product comprising ethanol, ethyl acetate, and water; separating at least a portion of the crude ethanol product in a first column at a first pressure into a first distillate comprising ethanol, ethyl acetate, and low concentrations of water, and a first residue comprising water, and separating at least a portion of the first distillate in a second column at a second pressure to yield an ethanol product stream and an ethyl acetate stream; wherein the second pressure is higher than the first pressure. In some embodiments, at least 95% of the acetic acid is converted in the reactor.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for recovering ethanol produced by hydrogenating acetic acid in the presence of a catalyst. The hydrogenation reaction produces a crude ethanol product that comprises ethanol, water, ethyl acetate, acetic acid, and other impurities including acetaldehyde, diethyl acetal and diethyl ether. To reduce capital costs, the processes of the current invention involve producing anhydrous ethanol products from a crude ethanol product without the use of a molecular sieve unit, such as a pressure-swing adsorption (PSA) unit, a membrane separation unit, or an entrainer. Since the location of the distillation boundary depends on the operating pressure, one may use two distillation columns, each operating at a different pressure, to produce anhydrous ethanol. In an alternative embodiment, one may use a single distillation column, alternating between different pressures.

The first distillation column is fed a liquid portion of the crude ethanol product. Typically, the crude ethanol product contains acetic acid, depending on the conversion in the reactor. Preferably, it is necessary to remove the acetic acid in the first distillation column from the ethanol. The first distillation column yields an overhead stream comprising ethanol and a residue comprising acetic acid. The first distillation column may operate at a pressure of less than 100 kPa, e.g., less than 80 kPa or less than 40 kPa. In terms of ranges, the first distillation column may operate at a pressure from 0.01 kPa to 100 kPa, e.g., from 0.01 kPa to 80 kPa or from 0.01 kPa to 40 kPa. Mild pressure conditions, from 20 kPa to 40 kPa, may be sufficient to remove achieve low concentrations of water in the first distillate and thus it is not required to use very low pressures that may require more energy. The first distillation column may operate to remove at least 90% of the acetic acid in the residue stream, e.g., at least 95%, substantially all or all of the acetic acid. The first distillation column may also operate to remove at least 60% of the water from the crude ethanol product, e.g., at least 70% of the water or at least 80% of the water. The first column may also separate organic components, including ethyl acetate, acetaldehyde, diethyl acetal and diethyl ether, with the ethanol in the first distillate. The amount of water in the first distillate may be minimized and is preferably less than 4.5 wt. %, or less than 3.5 wt. %. This amount of water would be less than the azeotropic amount of water in the binary mixture of ethanol and water at atmospheric pressure. Reducing the pressure of the first column may also further reduce the water concentration. For example, when the first distillation column is operated at approximately 32 kPa, the water concentration in the first distillate may be reduced to approximately 3.5 wt. %. When the first distillation column is operated at approximately 4 kPa, the water concentration in the first distillate may be reduced to 1 wt. %.

In some embodiments, a second distillation column may be present. The first distillate from the first column may be fed to the second column. Generally, the first distillate contains very low amounts of acetic acid. The residue stream from the second column may be used as the anhydrous ethanol product. For the present invention, the term "anhydrous" may be used to describe an ethanol product with less than 1 wt. % water. Anhydrous also covers lower amounts of water depending the ethanol specification. The second distillation column may operate at higher pressure than the first column. The second distillation column may be operated at a pressure of at least 200 kPa, e.g., at least 400 kPa or at least 600 kPa. In terms of ranges, the second distillation column may be operated at a pressure from 200 kPa to 2000 kPa, e.g., from 400 kPa to 2000 kPa or from 600 kPa to 2000 kPa. In one embodiment, the operating pressure of the second column may be 790 kPa. The water concentration of the residue stream when the second column is operated under a pressure of 790 kPa may be less than 0.15 wt. %. The ethyl acetate concentration in the residue stream may be less than 0.6 wt. %. The absolute concentrations of water and ethyl acetate in the residue product stream may depend on both the operating pressure and the concentration of other components in the feed. Without being bound by theory, the DEA may concentrate in the ethanol product when there is a low water concentration. If necessary, a subsequent separation may be used to remove DEA from the ethanol product. Advantageously, this separation approach results in an efficient process to recover ethanol, e.g., anhydrous ethanol, from the crude ethanol product.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. The third metal, when present, may be present in the catalyst in an amount from 0.05 to 20 wt. %, e.g. from 0.1 to 10 wt. %, or from 0.1 to 5 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 99 wt. %, or from 80 to 97.5 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be crystalline or amorphous.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Süd Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In a preferred embodiment, the conversion of acetic acid is at least 95, e.g., at least 98%, or at least 99%. In addition, the selectivity to ethanol may also be preferably high, and is preferably greater than 75%, e.g., greater than 85% or greater than 90%.

Ethanol Recovery

Figure 1:
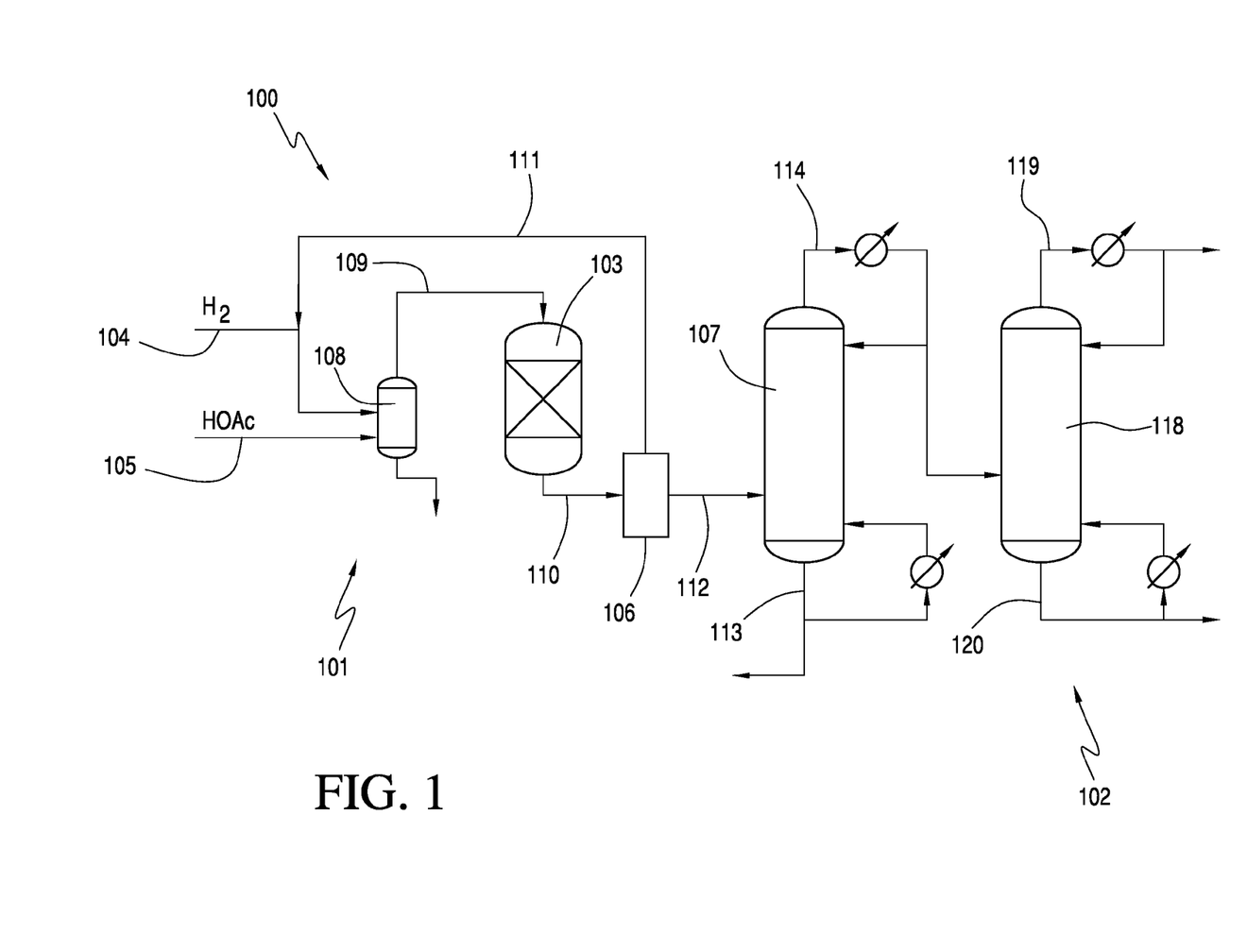
FIG. 1 is a schematic diagram of an ethanol production system for removing water from the ethanol product column in accordance with one embodiment of the present invention.

An exemplary ethanol recovery system in accordance with one embodiment of the present invention is shown in FIG. 1. Hydrogenation system 100 provides a suitable hydrogenation reactor and a process for separating ethanol from the crude reaction mixture according to one embodiment of the invention. System 100 comprises reaction zone 101 and separation zone 102. Reaction zone 101 comprises reactor 103, hydrogen feed line 104 and acetic acid feed line 105. Separation zone 102 comprises a separator 106 and distillation columns 107 and 118.

Hydrogen and acetic acid are fed to a vaporizer 108 via lines 104 and 105, respectively, to create a vapor feed stream in line 109 that is directed to reactor 103. In one embodiment, lines 104 and 105 may be combined and jointly fed to the vaporizer 108. The temperature of the vapor feed stream in line 109 is preferably from 100° C. to 350° C., e.g., from 120° C. to 310° C. or from 150° C. to 300° C. Any feed that is not vaporized is removed from vaporizer 108 and may be recycled or discarded. In addition, although line 109 is shown as being directed to the top of reactor 103, line 109 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid. In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 110.

The crude ethanol product in line 110 may be condensed and fed to a separator 106, which, in turn, provides a vapor stream 111 and a liquid stream 112. Suitable separators 106 include a flasher or a knockout pot. The separator 106 may operate at a temperature from 20° C. to 350° C., e.g., from 30° C. to 325° C. or from 60° C. to 250° C. The pressure of separator 106 may be from 100 kPa to 3000 kPa, e.g., from 125 kPa to 2500 kPa or from 150 to 2200 kPa. Optionally, the crude ethanol product in line 110 may pass through one or more membranes to separate hydrogen and/or other non-condensable gases.

The vapor stream 111 exiting separator 106 may comprise hydrogen and hydrocarbons, and may be purged and/or returned to reaction zone 101. As shown, vapor stream 111 is combined with the hydrogen feed 104 and co-fed to vaporizer 108. In some embodiments, the returned vapor stream 111 may be compressed before being combined with hydrogen feed 104.

The liquid stream 112 from separator 106 is withdrawn and pumped to the side of first column 107, also referred to as an "acid column." In one embodiment, the contents of liquid stream 112 are substantially similar to the crude ethanol product obtained from the reactor, except that the composition has substantially no hydrogen, carbon dioxide, methane or ethane, which are removed by the separator 106. Preferably, the crude ethanol product is not dehydrated prior to first column 107 by using an adsorption unit or membrane. Accordingly, liquid stream 112 may also be referred to as a crude ethanol product. Exemplary components of liquid stream 112 are provided in Table 2. It should be understood that liquid stream 112 may contain other components, not listed, such as components derived from the feed.

TABLE 2

COLUMN FEED COMPOSITION
(Liquid Stream 112)

| | Conc. (wt. %) | Conc. (wt. %) | Conc. (wt. %) |
|---|---|---|---|
| Ethanol | 5 to 72 | 15 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol, 2-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 110 or in liquid stream 112 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol.

Figure 2:
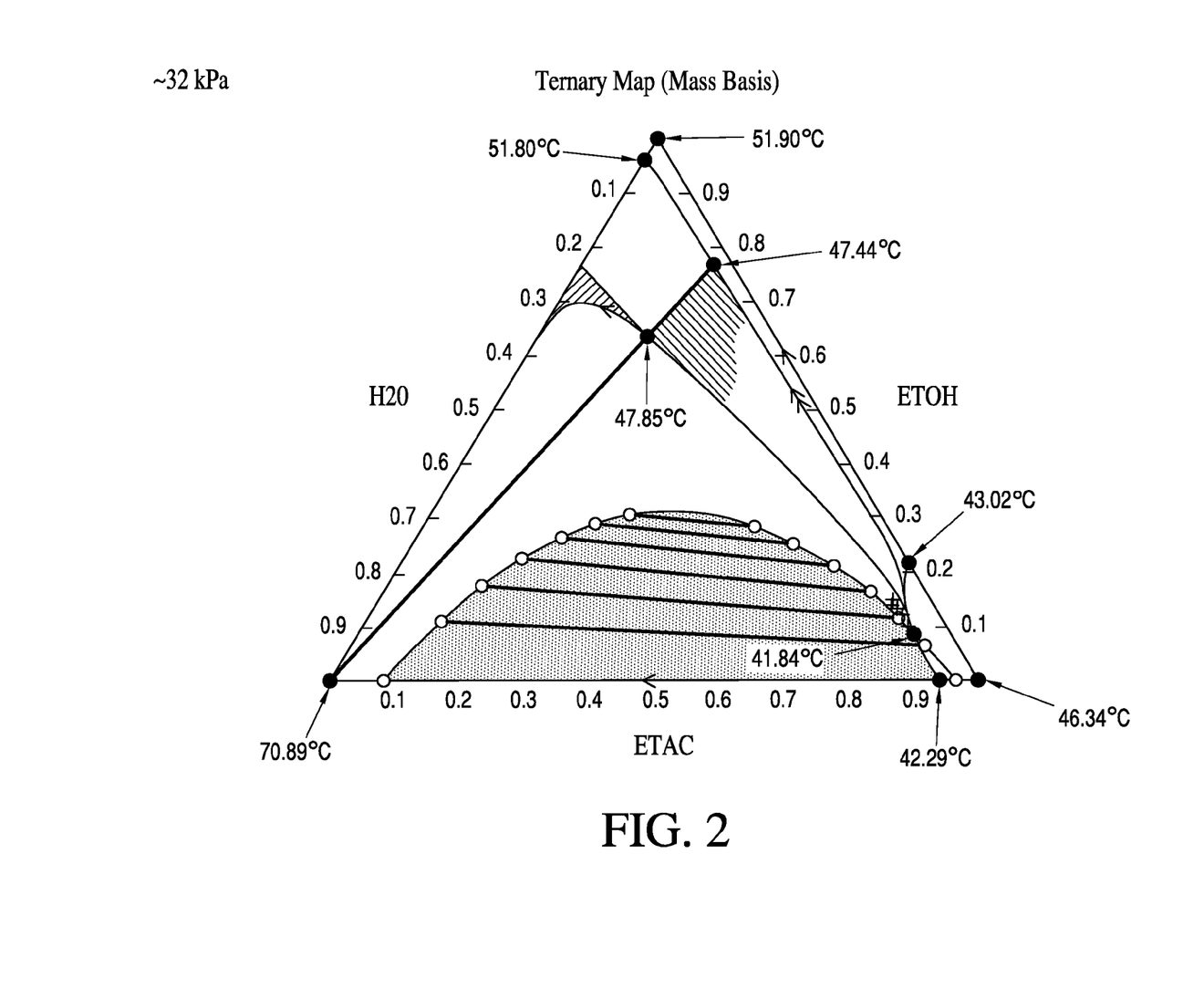
FIG. 2 is a phase diagram in a first column at a pressure of approximately 32 kPa.
Figure 3:
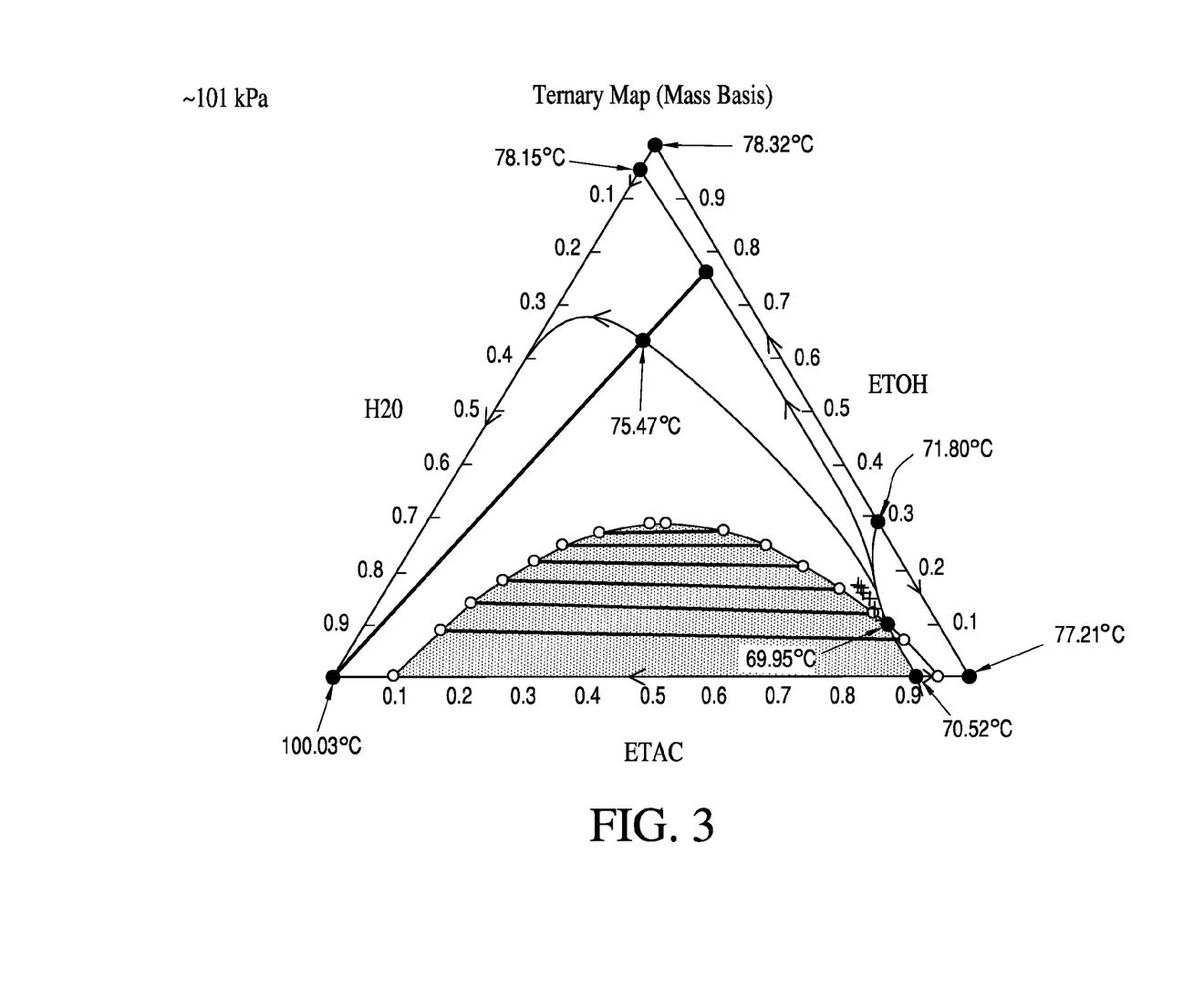
FIG. 3 is a phase diagram in a first column at a pressure of approximately 101 kPa.

Liquid stream 112 is preferably introduced in the lower part of first column 107, e.g., lower half or lower third. In some embodiments, liquid stream 112 may be fed above the mid-point of first column 107. The first distillation column may operate at a pressure of less than 100 kPa, e.g., less than 80 kPa or less than 40 kPa. In terms of ranges, the first distillation column may operate at a pressure from 0.01 kPa to 100 kPa, e.g., from 0.01 kPa to 80 kPa or from 0.01 kPa to 40 kPa. FIG. 2 shows a phase diagram for water, ethanol and ethyl acetate for column 107 at a pressure of 32 kPa. As compared to FIG. 3, which shows the phase diagram for column 107 at atmospheric pressure (101 kPa), the phase diagram at a pressure less than atmospheric may produce a first distillate that contains low amounts of water. The temperature of the first residue exiting in line 113, when the column is operated at 32 kPa, preferably is from 60° C. to 115° C., e.g., from 70° C. to 105° C. or from 80° C. to 100° C. The temperature of the first distillate ethyl in line 114 preferably is from 30° C. to 60° C., e.g., from 40° C. to 55° C. or from 45° C. to 55° C., when the column is operated at 32 kPa.

In one embodiment, no entrainers or azeotropic agents are added to first column 107. In first column 107, water and unreacted acetic acid, along with any other heavy components, if present, are removed from liquid stream 112 and are withdrawn, preferably continuously, as residue in line 113. First column 107 also forms an overhead distillate, which is withdrawn in line 114, and which may be condensed and refluxed, for example, at a ratio from 10:1 to 1:10, e.g., from 3:1 to 1:3 or from 1:2 to 2:1. In one embodiment, substantially all of the water in the crude ethanol product, e.g., at least 80%, 85%, or at least 90%, is removed in the first residue. The residue may comprise from 2.5 wt. % to 40 wt. % acetic acid, 60 wt. % to 99 wt. % water, and less than 0.5 wt. % ethanol. Acetic acid may be recovered from the residue and at least a portion of the acetic acid may be returned to the reactor. When the first residue comprises 0.01 wt. % to 10 wt. % acetic acid, the acetic acid may be neutralized or reacted. At least a portion of the water from the first residue may be returned to the reactor.

Exemplary components of the distillate and residue compositions for first column 107 are provided in Table 3 below. It should also be understood that the distillate and residue may also contain other components, not listed, such as components derived from the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN 107 | | | |
|---|---|---|---|
| | Conc. (wt. %) | Conc. (wt. %) | Conc. (wt. %) |
| Distillate | | | |
| Ethanol | 20 to 90 | 30 to 85 | 50 to 85 |
| Water | 0.01 to 4.5 | 0.5 to 4.2 | 1 to 3.5 |
| Acetic Acid | <1 | 0.001 to 1 | 0.01 to 0.5 |
| Ethyl Acetate | <60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| Residue | | | |
| Acetic Acid | <90 | 1 to 50 | 2.5 to 40 |
| Water | 60 to 100 | 85 to 99 | 92 to 98 |
| Ethanol | <1 | <0.9 | <0.5 |

In one embodiment, at high conversions of greater than 90%, acetic acid concentration in the residue may be less than 4 wt. %, e.g. from 0.5 to 3.5 wt. % or from 1 to 2.9 wt. %.

Some species, such as acetals, may decompose in column 107 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This reaction may be regulated using the residence time and/or temperature of crude ethanol product.

The composition of the residue stream may vary depending on acetic acid conversion as well as the composition of the crude ethanol product and separation conditions in the first column. Depending on the amount of water and acetic acid contained in the residue of first column 107, line 113 may be treated in one or more of the following processes: (i) entirely or partially recycled to the hydrogenation reactor, (ii) separated into acid and water streams, (iii) treated with a solvent in a weak acid recovery process, (iv) reacted with an alcohol to consume the unreacted acetic acid, or (v) disposed to a waste water treatment facility. The following are exemplary processes for further treating first residue and it should be understood that any of the following may be used regardless of acetic acid concentration.

When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where residue in line 113 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 113 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. % or less than 1 wt. %, the residue may be neutralized and/or diluted before being disposed of to a waste water treatment facility. The organic content, e.g., acetic acid content, of the residue beneficially may be suitable to feed microorganisms used in a waste water treatment facility.

The distillate in line 114 preferably comprises ethanol and ethyl acetate. The final ethanol product may be derived from the distillate in line 114. In one embodiment, the weight ratio of water in the residue to the water in the distillate is greater than 1:1, e.g., greater than 2:1 or greater than 4:1. In addition, the weight ratio of acetic acid in the residue to acetic acid in the distillate is optionally greater than 10:1, e.g., greater than 15:1 or greater than 20:1. Preferably, the distillate in line 114 is substantially free of acetic acid and may contain, if any, only trace amounts of acetic acid. In some embodiments, the distillate comprises 20 wt. % to 90 wt. % ethanol, 0.01 wt. % to 60 wt. % ethyl acetate, and from 0.01 wt. % to 4.5 wt. % water. The distillate in line 114 may comprise from 0.01 wt. % to 10 wt. % acetic acid, e.g., less than 0.5 wt. % acetic acid or less than 600 wppm acetic acid.

Suitable columns for use in one embodiment of the present invention may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler.

Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures employed in the column may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

In FIG. 1, the distillate in line 114 comprises ethanol, ethyl acetate, and other organics such as acetaldehyde. In some embodiments, such distillate compositions may be possible at higher selectivities to ethanol, for example, selectivities of greater than 90%, greater than 95% or greater than 97%. The amount of water in the distillate of line 114 is less than 4.5 wt. %. Preferably, the distillate in line 114 is not dehydrated using an adsorption unit or membrane.

As shown, the first distillate in line 114 is fed to a second column 118, also referred to as an "ethanol product column," for separating the first distillate into an ethanol product stream in line 120 and an ethyl acetate stream in second distillate in line 119. The first distillate in line 114 may be preferably introduced into the middle part or upper part of column 118.

Figure 4:
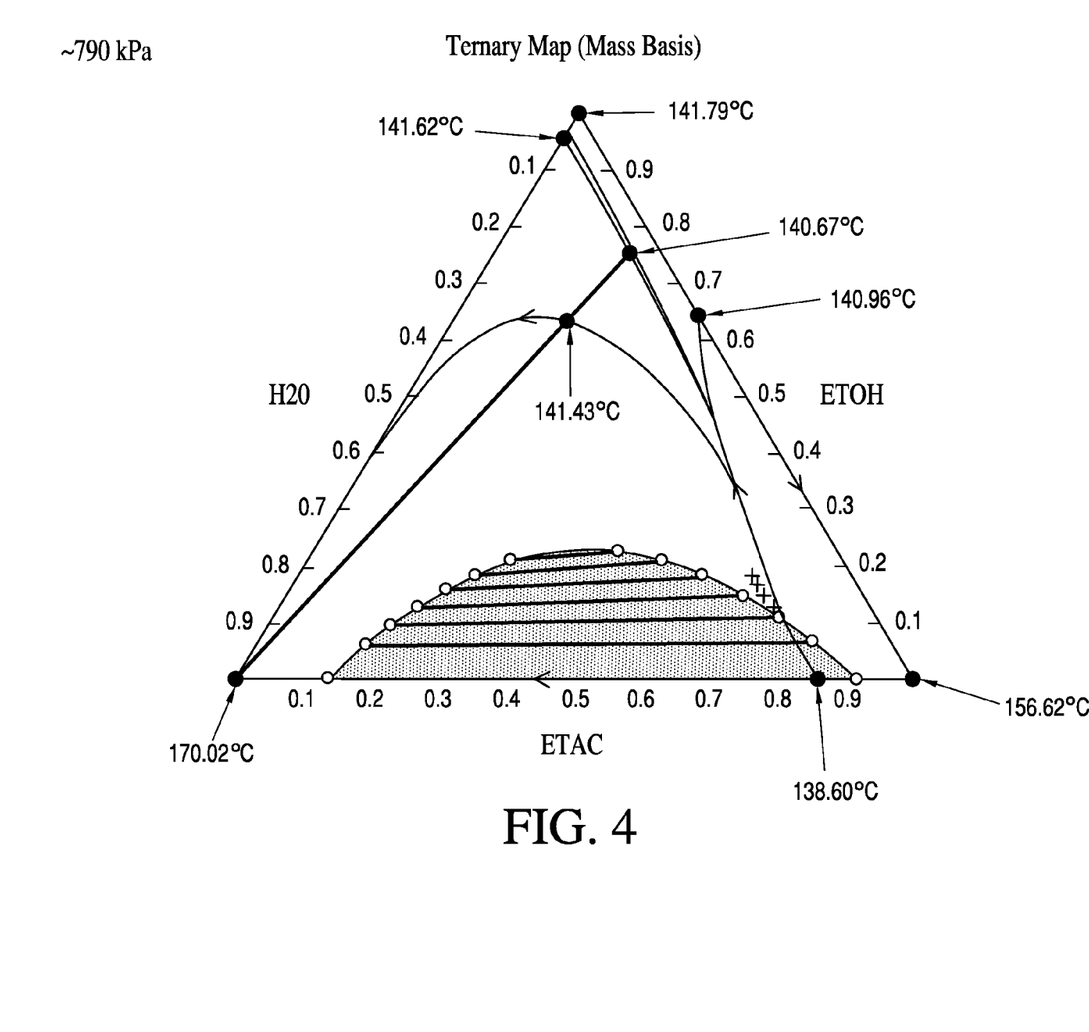
FIG. 4 is a phase diagram in a second column at a pressure of approximately 790 kPa.
Figure 5:
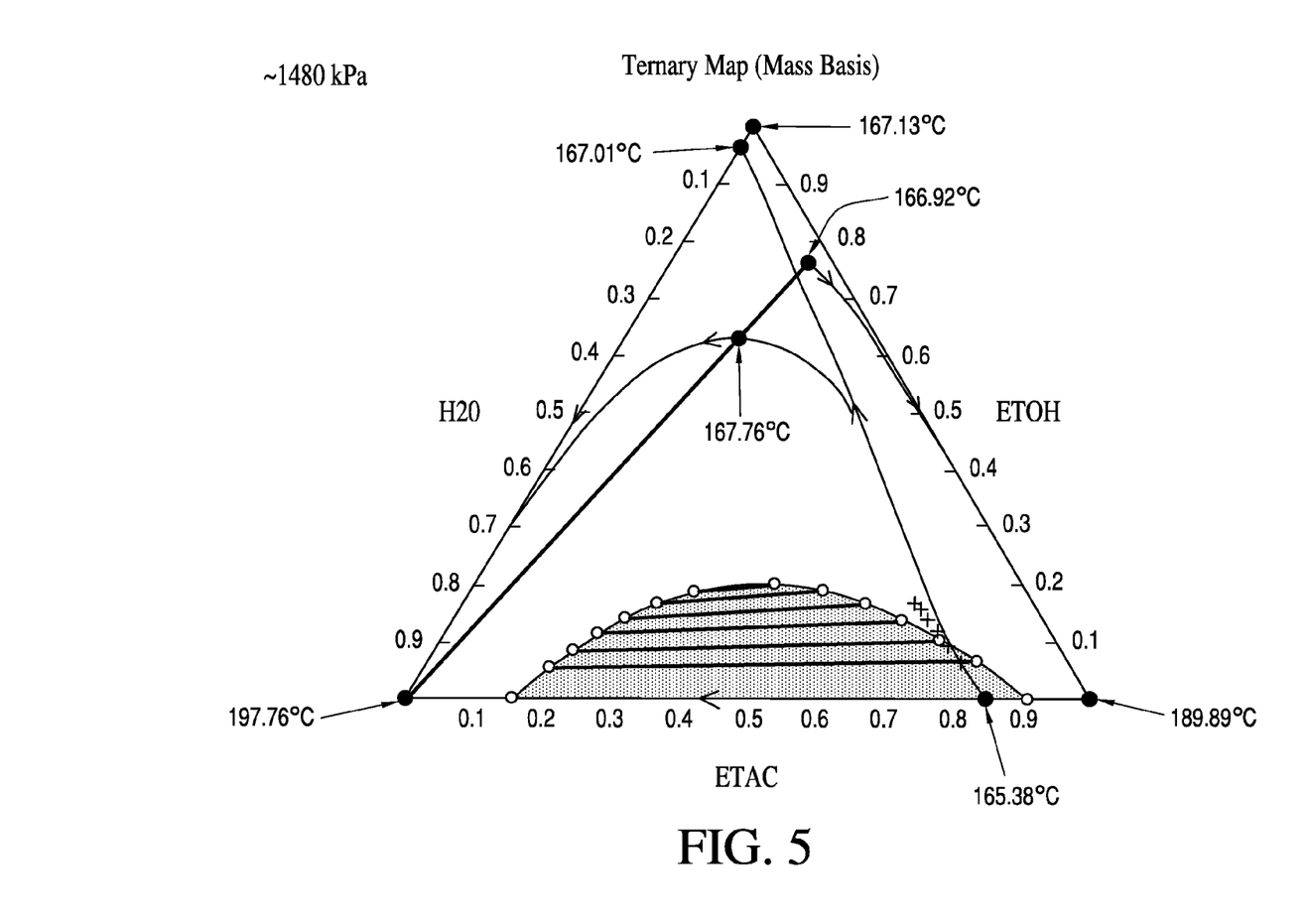
FIG. 5 is a phase diagram in a second column at a pressure of approximately 1480 kPa.

Preferably, the pressure of second column 118 is higher than the pressure of first column 107. Second column 118 may be operated at a pressure of at least 200 kPa, e.g., at least 400 kPa or at least 600 kPa. In terms of ranges, the second distillation column may be operated at a pressure from 200 kPa to 2000 kPa, e.g., from 400 kPa to 2000 kPa or from 600 kPa to 2000 kPa. The pressure of second column 118 is preferably at least 100 kPa higher than the pressure of first column 107. FIG. 4 shows the phase diagram for column 118 at 790 kPa. FIG. 5 shows the phase diagram for column 118 at 1480 kPa. The distillate boundaries at higher pressures in column 118 may allow for recovery of ethanol with low amounts of water. In some embodiments, second column 118 does not contain any entrainers or azeotropic agents.

Ethanol product column 118 is preferably operates above atmospheric pressure. The residue in line 120 may be referred to as the "ethanol product stream." The temperature of the ethanol product stream exiting in line 120, when the column is operated at 790 kPa, preferably is from 140° C. to 170° C., e.g., from 140° C. to 160° C. or from 145° C. to 155° C. The temperature of the ethyl acetate stream in line 119 preferably is from 100° C. to 139° C., e.g., from 110° C. to 138° C. or from 120° C. to 138° C., when the column is operated at 790 kPa. The ethanol product stream does not require further dehydration using an adsorption unit or membrane.

Exemplary components of the distillate and residue compositions for second column 118 are provided in Table 4 below. It should also be understood that the distillate and residue may also contain other components, not listed, such as components derived from the feed.

TABLE 4

SECOND COLUMN 118

|  | Conc. (wt. %) | Conc. (wt. %) | Conc. (wt. %) |
|---|---|---|---|
| Distillate |  |  |  |
| Ethanol | 30 to 70 | 35 to 65 | 40 to 60 |
| Ethyl Acetate | 30 to 70 | 35 to 65 | 40 to 60 |
| Water | 1 to 20 | 1 to 15 | 1 to 10 |
| Acetaldehyde | <10 | 0.1 to 5 | 1 to 3 |
| Diethyl Acetal | <1 | <0.5 | <0.01 |
| Acetone | <1 | <0.5 | <0.01 |
| Acetic Acid | <0.05 | <0.03 | <0.02 |
| Residue |  |  |  |
| Ethanol | 70 to 99.9 | 80 to 99.5 | 85 to 99.1 |
| Water | <4.5 | 0.01 to 4.2 | 0.1 to 3.5 |
| Ethyl Acetate | <1.5 | 0.01 to 1 | 0.1 to 0.7 |
| Diethyl Acetal | <2 | 0.01 to 1 | 0.1 to 0.5 |
| Acetic Acid | <1 | <0.5 | <0.01 |

In one aspect, not shown, the ethyl acetate stream or a portion thereof in line 119 may be returned to reactor 103. In another aspect the ethyl acetate stream may also be purged in part and removed as an ethyl acetate solvent product and in other aspects ethyl acetate stream may be returned to first column 107 in part. The ethyl acetate and/or acetaldehyde in the ethyl acetate stream may be further reacted in hydrogenation reactor 103 or in an secondary reactor. The outflow from the secondary reactor may be fed to reactor 103 to produce additional ethanol or to a distillation column, such as columns, 107, or 118, to recover additional ethanol.

The ethanol product stream in line 120 may be an industrial grade ethanol comprising from 96 to 99.5 wt. % ethanol, e.g., from 96 to 99 wt. % or from 96 to 98 wt. % ethanol, based on the total weight of the ethanol product. The finished ethanol composition may comprise less than 4.5 wt. % water, less than 0.01 wt. % ethyl acetate and less than 0.01 wt. % acetic acid. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 96 to 99.9 | 96 to 99.5 | 96 to 98.5 |
| Water | <4.5 | 0.01 to 4.2 | 0.1 to 3.5 |
| Acetic Acid | <1 | <0.1 | <0.01 |
| Ethyl Acetate | <1.5 | <1 | <0.7 |
| Acetal | <2 | 0.005 to 1 | 0.01 to 0.5 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882, 244 and zeolite Y in U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

Example

The following examples were prepared with ASPEN Plus 7.1 simulation software to test various feed composition and separation systems.

The hydrogenation of acetic acid was conducted in accordance with the hydrogenation process of the present invention as shown in FIG. 1. Crude ethanol product in liquid stream 112 was fed to first column 107. The components of crude ethanol product in liquid stream 112 are shown below in Table 6.

TABLE 6

COLUMN FEED COMPOSITION
(Liquid Stream 112)

|  | Conc. (wt. %) |
|---|---|
| Ethanol | 61.9 |
| Acetic Acid | 0.6 |
| Water | 19.3 |
| Ethyl Acetate | 16.9 |
| Acetaldehyde | 0.9 |
| Diethyl Acetal | 0.5 |
| Diethyl Ether | <0.01 |

Liquid stream 112 was fed to first column 107. The pressure at the top of first column 107 was 32.4 kPa and temperature was 46.2° C. The distillate and residue compositions from first column 107 are shown below in Table 7.

TABLE 7

FIRST COLUMN 107

| Distillate | Conc. (wt. %) | Residue | Conc. (wt. %) |
|---|---|---|---|
| Ethanol | 74.6 | Ethanol | <0.01 |
| Water | 3.5 | Water | 96.5 |
| Acetic Acid | <0.01 | Acetic Acid | 3.5 |
| Ethyl Acetate | 20.3 | Ethyl Acetate | — |
| Acetaldehyde | 1.1 | Acetaldehyde | — |
| Diethyl Acetal | 0.6 | Diethyl Acetal | — |
| Diethyl Ether | <0.01 | Diethyl Ether | <0.01 |

The distillate exiting first column 107 was fed to second column 118 via line 114. The pressure at the top of the second column was 790 kPa. The distillate and residue compositions from second column 118 are shown below in Table 8.

TABLE 8

SECOND COLUMN 118

| Distillate | Conc. (wt. %) | Residue | Conc. (wt. %) |
|---|---|---|---|
| Ethanol | 45.6 | Ethanol | 98.3 |
| Water | 7.6 | Water | 0.1 |
| Acetic Acid | — | Acetic Acid | <0.01 |
| Ethyl Acetate | 44.5 | Ethyl Acetate | 0.6 |
| Acetaldehyde | 2.4 | Acetaldehyde | —% |
| Diethyl Acetal | 0.05 | Diethyl Acetal | 1 |
| Diethyl Ether | <0.01 | Diethyl Ether | — |

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
    hydrogenating acetic acid from an acetic acid feed stream in a reactor to form a crude ethanol product comprising ethanol, ethyl acetate, acetic acid, and water;
    separating at least a portion of the crude ethanol product in a first column at a first pressure into a first distillate comprising ethanol, ethyl acetate, and low concentration of water, and a first residue comprising from 2.5 to 40 wt. % acetic acid, from 60 to 99 wt. % water, and less than 0.5 wt. % ethanol, and
    separating at least a portion of the first distillate in a second column at a second pressure to yield an ethanol product stream and an ethyl acetate stream;
    wherein the second pressure is higher than the first pressure and;
    wherein the first distillate is not dehydrated using an adsorption unit or membrane.

2. The process of claim 1, wherein the second pressure is greater than atmospheric pressure.

3. The process of claim 1, wherein the second pressure is from 200 kPa to 2,000 kPa.

4. The process of claim 1, wherein the first pressure is from 0.01 kPa to 80 kPa.

5. The process of claim 1, wherein the second pressure is at least 100 kPa higher than the first pressure.

6. The process of claim 1, wherein at least 60% of the water in the crude ethanol product is removed in the first residue stream.

7. The process of claim 1, wherein the low concentration of water is less than 4.5 wt. %.

8. The process of claim 1, wherein the first distillate comprises from 20 to 90 wt. % ethanol, from 0.01 to 4 wt. % water and from 0.01 to 60 wt. % ethyl acetate.

9. The process claim 1, wherein the first distillate comprises less than 600 wppm acetic acid.

10. The process of claim 1, wherein no azeotropic agents and/or entrainers are added to the first column or the second column.

11. The process of claim 1, wherein the ethanol product stream comprises from 96 to 99.5 wt. % ethanol and from 0.01 to 4 wt. % water.

12. The process of claim 1, wherein the crude ethanol product is not dehydrated using an adsorption unit or membrane.

13. The process of claim 1, wherein the ethanol product stream is not dehydrated using an adsorption unit or membrane.

14. The process of claim 1, wherein the ethyl acetate stream is returned to the reactor.

15. The process of claim 1, further comprising recovering acetic acid from the first residue and returning at least a portion of the recovered acetic acid to the reactor.

16. The process of claim 1, further comprising returning at least a portion of the first residue to the reactor.

17. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

18. A process for producing ethanol, comprising the steps of:
    hydrogenating acetic acid from an acetic acid feed stream in a reactor to form a crude ethanol product consisting of a) ethanol, b) ethyl acetate, c) acetaldehyde, d) water and e) one or more compounds selected from the group consisting of:
    1) esters selected from the group consisting of ethyl propionate, methyl acetate, isopropyl acetate, n-propyl acetate, n-butyl acetate, and mixtures thereof,
    2) ethers selected from the group consisting of diethyl ether, methyl ether, isobutyl ethyl ether, and mixtures thereof,
    3) alcohols selected from the group consisting of methanol, isopropanol, n-propanol, n-butanol, 2-butanol, and mixtures thereof,
    4) acetal, and
    5) acetone;
    separating at least a portion of the crude ethanol product in a first column at a first pressure into a first distillate comprising ethanol, ethyl acetate, and low concentration of water, and a first residue comprising water, and
    separating at least a portion of the first distillate in a second column at a second pressure to yield an ethanol product stream and an ethyl acetate stream;
    wherein the second pressure is higher than the first pressure and;
    wherein the first distillate is not dehydrated using an adsorption unit or membrane.

* * * * *